United States Patent [19]

Morita et al.

[11] Patent Number: 4,756,743

[45] Date of Patent: Jul. 12, 1988

[54] HERBICIDAL COMPOSITION

[75] Inventors: Kouichi Morita, Toyonaka; Ryo Yoshida, Kawanishi, both of Japan

[73] Assignee: Sumitomo Chemical Company, Limited, Osaka, Japan

[21] Appl. No.: 796,898

[22] Filed: Nov. 12, 1985

[30] Foreign Application Priority Data

Nov. 13, 1984 [JP] Japan .................................. 59-238856

[51] Int. Cl.[4] ............................................ A01N 43/54
[52] U.S. Cl. ............................................ 71/92; 71/96
[58] Field of Search ...................................... 71/92, 96

[56] References Cited

FOREIGN PATENT DOCUMENTS 16181 6/1983 Australia .
0083055 7/1983 European Pat. Off. .

Primary Examiner—Catherine L. Mills
Attorney, Agent, or Firm—Birch, Stewart, Kolasch & Birch

[57] ABSTRACT

A herbicidal composition which comprises as the active ingredients (a) 2-(4-chloro-2-fluoro-5-n-pentyloxycarbonylmethoxyphenyl)-4,5,6,7-tetrahydro-2H-isoindole-1,3-dione and (b) ethyl [[[[2-(4-chloro-6-methoxypyrimidin-2-yl)amino]carbonyl]amino]sulfonyl]benzoate, and an inert carrier or diluent. The composition exerts an enhanced herbicidal potency.

6 Claims, 1 Drawing Sheet

HERBICIDAL COMPOSITION

BACKGROUND OF THE INVENTION

1. Field of the Invention

The present invention relates to a herbicidal composition. More particularly, it relates to a herbicidal composition comprising as the active ingredients (a) 2-(4-chloro-2-fluoro-5-n-pentyloxycarbonylmethoxyphenyl)-4,5,6,7-tetrahydro-2H-isoindole-1,3-dione (hereinafter referred to as "Compound (I)") of the formula:

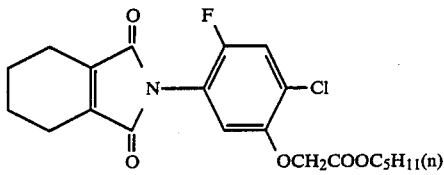

and (b) ethyl 2-[[[[(4-chloro-6-methoxypyrimidin-2-yl)-amino]carbonyl]amino]sulfonyl]benzoate (hereinafter referred to as "Compound (II)") of the formula:

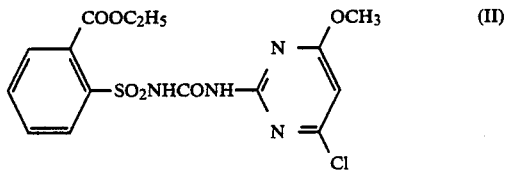

which exerts a highly enhanced herbicidal activity against a wide variety of weeds without causing any material phytotoxicity to crop plants, particularly to peanut and soybean.

2. Discussion of Related Art

In recent years, a great number of chemicals having herbicidal activity have been used to exterminate or control the undesired vegetation of weeds. Since, weeds are diversified in types and, the growth of weeds extends for a long duration the herbicidal effects of conventional herbicidal agents are quite restricted. Consequently, the appearance of any herbicidal agent which exerts a strong herbicidal activity against a wide variety of weeds without any material phytotoxicity to crop plants has been highly demanded.

SUMMARY OF THE INVENTION

As a result of the extensive study, it has now been found that the associated use of Compounds (I) and (II) as the active ingredients produces a highly enhanced herbicidal activity against a wide variety of weeds without causing any material phytotoxicity to crop plants, particularly peanut or soybean. In comparison with the sole use of each of said active ingredients, enhancement of the herbicidal potency on their associated use is remarkable so that the active ingredient may be applied in a smaller dosage. Thus, a clear and definite synergistic effect is observed in the associated use.

The herbicidal composition of the invention which comprises Compounds (I) and (II) can exterminate or control a variety of weeds, i.e. dicotyledonous weeds such as common lambsquarters (*Chenopodium album*), redroot pigweed (*Amaranthus retroflexus*), field bindweed (*Convolvulus arvensis*), common purslane (*Portulaca oleracea*), common cocklebur (*Xanthium strumarium*), jimsonweed (*Datura stramonium*) and velvetleaf (*Abutilon theophrasti*), Ipomoea plants such as tall morningglory (*Ipomoea purpurea*), hemp sesbania (*Sesbania exaltata*), prickly sida (*Sida spinosa*), black nightshade (*Solanum nigrum*) and common sunflower (*Helianthus annuus*), monocotyledonous weeds such as green foxtail (*Setaria viridis*), southern crabgrass (*Digitaria ciliaris*), barnyardgrass (*Echinochloa crus-galli*) and johnsongrass (*Sorghum halepense*), quackgrass (*Agropyron repens*), etc. Particularly, it is advantageous that the herbicidal composition of the invention is useful in simultaneous control of such weeds as hemp sesbania, prickly sida, tall morningglory, velvetleaf and common cocklebur which are hardly exterminated.

Compound (I) is known to exert a herbicidal activity (EP-A No. 0083055). Compound (II) is also known to be useful as a herbicide (Australian Patent Application No. 16181/83). However, the associated use of Compounds (I) and (II) has never been attempted, and the production of said synergistic effect on such associated use has never been expected.

The proportion of Compounds (I) and (II) as the active ingredients in the composition of the invention may vary within a considerable broad range. Generally, however, Compound (II) may be used in an amount of 0.001 to 10 part(s) by weight, preferably of 0.005 to 2 part(s) by weight, to one part by weight of Compound (I).

In addition to the above active ingredients, the composition may contain a solid or liquid carrier or diluent. Any surface active or auxiliary agent may be also incorporated therein. Thus, the composition may be formulated in any conventional preparation form such as emulsifiable concentrate, wettable powder or suspension. The combined content of the active ingredients in the composition may be from 0.5 to 90% by weight, preferably from 2 to 80% by weight.

As the solid carrier or diluent, there may be used kaolin clay, attapulgite clay, bentonite, terra alba, pyrophyllite, talc, diatomaceous earth, calcite, wallnut-shell powder, urea, ammonium sulfate, synthetic hydrated silica, etc. Examples of the liquid carrier or diluent are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton-seed oil), dimethylsulfoxide, acetonitrile, water, etc.

The surface active agent used for emulsification, dispersion or spreading may be any of the anionic and nonionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

DETAILED DESCRIPTION OF THE INVENTION

Figure 1:
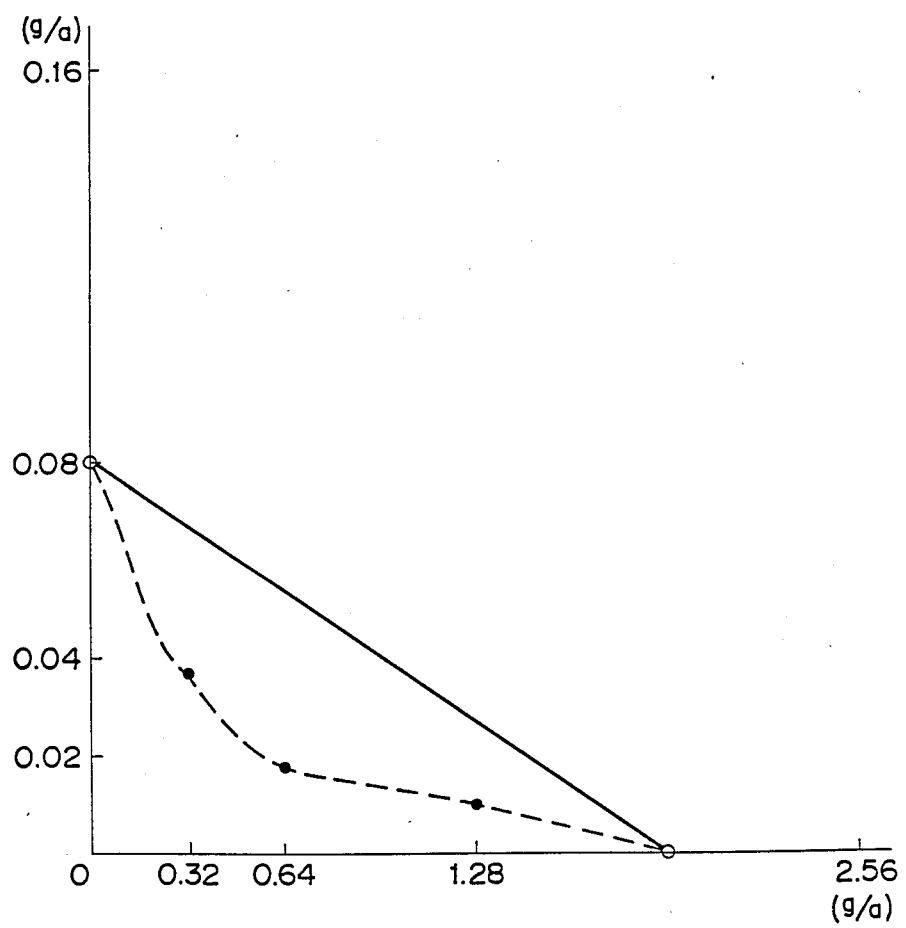

Practical embodiments for preparation of the composition are illustratively shown in the following Formulation Examples wherein part(s) are by weight.

FORMULATION EXAMPLE 1

Ten parts of Compound (I), 10 parts of Compound (II), 10 parts of synthetic hydrated silica, 3 parts of alkylsulfonate, 2 parts of calcium ligninsulfonate and 65 parts of diatomaceous earth are well mixed while being powdered to obtain a wettable powder.

FORMULATION EXAMPLE 2

Five parts of Compound (I), 20 parts of Compound (II), 3 parts of polyoxyethylene sorbitan monooleate, 3 parts of CMC and 69 parts of water are mixed and pulverized until the particle size of the composition become less than 5 microns to obtain suspensions.

FORMULATION EXAMPLE 3

Forty parts of Compound (I), 40 parts of Compound (II), 3 parts of calcium ligninsulfonate, 2 parts of sodium laurylsulfate and 15 parts of synthetic hydrated silicon dioxide are well mixed while being powdered to obtain a wettable powder.

FORMULATION EXAMPLE 4

1.5 parts of Compound (I), 0.5 part of Compound (II), 1 part of polyoxyethylene sorbitan monooleate, 5 parts of polyvinyl alcohol and 92 parts of water are mixed and pulverized until the particle size of the composition become less than 5 microns to obtain suspensions.

A composition comprising Compound (I) and Compound (II) thus formulated is useful for post-emergence control of undesired weeds by foliar treatment. The foliar treatment may be effected by spraying the composition containing Compound (I) and Compound (II) over the top of plants. The direct application may be also adopted.

In order to improve the herbicidal activity, the composition may be used with other herbicides. Besides, it may be used in combination with insecticides, acaricides, nematocides, fungicides, plant growth regulators, fertilizers, soil improvers, etc.

The dosage of the active ingredients may vary depending on prevailing weather conditions, soil involved, formulation used, mixing proportion of each active ingredient, crop and weed species, etc. In general, however, the total amount of Compounds (I) and (II) are favored to be within a range of 0.2 to 4 grams per are.

In case of the composition being formulated into an emulsifiable concentrate, wettable powder or suspension, it is normally diluted with water and applied over the top at a volume of 1 to 10 liters per are to the foliage of the crop plants or weeds which germinate or have germinated. The dilution may include, in addition to the above mentioned surface active agent, any spreading or auxiliary agent such as polyoxyethylene resin acid esters, ligninsulfonates, abietic acid, dinaphthylmethanedisulfonates, paraffin and the like.

The practical herbicidal activity of the system of the invention will be explained in further detail with reference to the following Test Examples wherein the growth controlling percentage (%) was determined by weighing the aerial parts of the test plants (fresh weight) and making calculation according to the following equation:

$$\text{Growth controlling percentage (\%)} = \left\{ 1 - \frac{\text{Fresh weight of test plant in treated plot}}{\text{Fresh weight of test plant in untreated plot}} \right\} \times 100$$

The phytotoxicity to crop plants was visually observed.

TEST EXAMPLE 1

Seeds of hemp sesbania, prickly sida, tall morningglory, velvetleaf, common cocklebur and soybean were sowed in a concrete pot ($40 \times 35$ cm$^2$, 35 cm (H)) filled with field soil and the test plants were grown for 15 days in outdoors. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 21 days' cultivation in outdoors, the growth controlling percentage was observed. The results are shown in Table 1. At the time of treatment, the test plants were in general at the stage of 4 to 8-leaf stage, although the growing stage varied depending on each species.

TABLE 1

| Compound No. | Dosage (g/a) | Mixing ratio | Growth controlling percentage (%) | | | | | Phytotoxicity Soybean |
|---|---|---|---|---|---|---|---|---|
| | | | Hemp sesbania | Prickly sida | Tall morning-glory | Velvet-leaf | Common cock-lebur | |
| Compound (I) | 4 | — | 100 | 100 | 93 | 95 | 100 | None |
| | 2 | — | 90 | 100 | 85 | 95 | 100 | None |
| | 1 | — | 75 | 93 | 83 | 93 | 83 | None |
| | 0.5 | — | 40 | 90 | 68 | 85 | 75 | None |
| | 0.2 | — | 13 | 73 | 40 | 85 | 40 | None |
| Compound (II) | 0.3 | — | 43 | 30 | 90 | 96 | 100 | None |
| | 0.1 | — | 30 | 0 | 75 | 85 | 90 | None |
| | 0.05 | — | 10 | 0 | 70 | 75 | 90 | None |
| | 0.02 | — | 0 | 0 | 60 | 50 | 80 | None |
| | 0.01 | — | 0 | 0 | 35 | 30 | 51 | None |
| Compound (I) + Compound (II) | 0.2 + 0.01 | 20:1 | 40 | 79 | 85 | 98 | 98 | None |
| | 0.2 + 0.02 | 10:1 | 43 | 80 | 99 | 100 | 100 | None |
| | 0.2 + 0.05 | 4:1 | 58 | 80 | 100 | 100 | 100 | None |
| | 0.2 + 0.1 | 2:1 | 69 | 82 | 100 | 100 | 100 | None |
| | 0.5 + 0.01 | 50:1 | 57 | 95 | 93 | 100 | 100 | None |
| | 0.5 + 0.02 | 25:1 | 60 | 95 | 99 | 100 | 100 | None |
| | 0.5 + 0.05 | 10:1 | 75 | 97 | 100 | 100 | 100 | None |
| | 0.5 + 0.1 | 5:1 | 86 | 99 | 100 | 100 | 100 | None |
| | 1 + 0.01 | 100:1 | 79 | 99 | 99 | 100 | 100 | None |
| | 1 + 0.02 | 50:1 | 82 | 100 | 100 | 100 | 100 | None |
| | 1 + 0.05 | 20:1 | 95 | 100 | 100 | 100 | 100 | None |

TABLE 1-continued

| Compound No. | Dosage (g/a) | Mixing ratio | Growth controlling percentage (%) | | | | | Phyto-toxicity Soybean |
| --- | --- | --- | --- | --- | --- | --- | --- | --- |
| | | | Hemp sesbania | Prickly sida | Tall morning-glory | Velvet-leaf | Common cock-lebur | |
| | 1 + 0.1 | 10:1 | 97 | 100 | 100 | 100 | 100 | None |
| | 2 + 0.01 | 200:1 | 100 | 100 | 100 | 100 | 100 | None |
| | 2 + 0.02 | 100:1 | 100 | 100 | 100 | 100 | 100 | None |
| | 2 + 0.05 | 40:1 | 100 | 100 | 100 | 100 | 100 | None |
| | 2 + 0.1 | 20:1 | 100 | 100 | 100 | 100 | 100 | None |
| Untreated | | | 0 | 0 | 0 | 0 | 0 | None |

TEST EXAMPLE 2

Seeds of black nightshade, field bindweed, redroot pigweed, velvetleaf and peanut were sowed in a concrete pot (40×35 cm$^2$, 35 cm (H)) filled with field soil and the test plants were grown for 22 days in outdoors. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 20 days' cultivation in outdoors, the growth controlling percentage was observed. The results are shown in Table 2. At the time of treatment, the test plants were in general at the stage of 1 to 5-leaf stage and in 2 to 13 cm height, although the growing stage varied depending on each species.

TABLE 2

| Compound No. | Dosage (g/a) | Mixing ratio | Growth controlling percentage (%) | | | | Phyto-toxicity Peanut |
| --- | --- | --- | --- | --- | --- | --- | --- |
| | | | Black nightshade | Field bindweed | Redroot pigweed | Velvet-leaf | |
| Compound (I) | 1.2 | — | 100 | 98 | 100 | 100 | None |
| | 0.4 | — | 89 | 80 | 85 | 100 | None |
| | 0.13 | — | 80 | 70 | 70 | 85 | None |
| Compound (II) | 0.18 | — | 60 | 75 | 100 | 90 | None |
| | 0.06 | — | 40 | 55 | 45 | 78 | None |
| | 0.02 | — | 30 | 40 | 20 | 28 | None |
| Compound (I) + Compound (II) | 0.13 + 0.02 | 13:2 | 100 | 100 | 90 | 100 | None |
| | 0.13 + 0.06 | 13:6 | 100 | 100 | 98 | 100 | None |
| | 0.13 + 0.18 | 13:18 | 100 | 100 | 100 | 100 | None |
| | 0.4 + 0.02 | 20:1 | 100 | 100 | 100 | 100 | None |
| | 0.4 + 0.06 | 20:3 | 100 | 100 | 100 | 100 | None |
| | 0.4 + 0.18 | 20:9 | 100 | 100 | 100 | 100 | None |
| | 1.2 + 0.02 | 10:1 | 100 | 100 | 100 | 100 | None |
| | 1.2 + 0.06 | 10:3 | 100 | 100 | 100 | 100 | None |
| | 1.2 + 0.18 | 10:9 | 100 | 100 | 100 | 100 | None |
| Untreated | | | 0 | 0 | 0 | 0 | None |

TEST EXAMPLE 3

Seeds of tall morningglory were sowed in a plastic pot (11×15 cm$^2$, 7 cm (H)) filled with field soil and the test plant was grown for 26 days in outdoors. A designed amount of the composition in the form of a wettable powder formulated as in Formulation Example 1 was diluted with water and sprayed to the foliage of the test plant at a spray volume of 5 liters per are by the aid of a small hand sprayer. After 18 days' cultivation in outdoors, the growth controlling percentage was observed. The results are shown in Table 3. At the time of treatment, the test plant was 3-leaf stage and in 14 cm height.

TABLE 3

| Dosage of Compound (II) (g/a) | Dosage of Compound (I) (g/a) | | | | |
| --- | --- | --- | --- | --- | --- |
| | Growth controlling percentage (%) | | | | |
| | 0 | 0.32 | 0.64 | 1.28 | 2.56 |
| 0 | 0 | 20 | 60 | 80 | 100 |
| 0.02 | 35 | 70 | 95 | 100 | 100 |
| 0.04 | 75 | 95 | 100 | 100 | 100 |
| 0.08 | 90 | 100 | 100 | 100 | 100 |
| 0.16 | 100 | 100 | 100 | 100 | 100 |

The above test results were analyzed according to the equivalent efficacy streaking method (cf. Hideo Chisaka: "Noyaku Jikkenho" (Agricultural Expeirmental Method), Chapter 3: Herbicides, pages 109–116). Namely, several combinations of the compositions having different mixing ratio of Compounds (I) and (II) but exerting the same level of growth controlling effect, for example, 90% growth control, were analyzed and plotted in a graph so as to readily determine a synergistic effect, arithmetic effect or competitive effect. In case of enhancing the synergistic effect, the equivalent efficacy line as plotted is shown below the arithmetic efficacy line.

As shown in FIG. 1 of the accompanying drawing wherein the ordinate indicates the dosage of Compound (II) per are and the abscissa indicates the dosage of Compound (I) per are, the equivalent efficacy line (e.g. dotted line) of 90% growth control of tall morningglory is located under the arithmetic efficacy line (e.g. solid line), from which it is presumed revealed that the associated use of Compounds (I) and (II) in certain mixing ratio would enhance the synergistic effect.

What is claimed is:

1. A herbicidal composition which consists essentially of a herbicidally effective amount of the active ingredients (a) 2-(4-chloro-2-fluoro-5-n-pentyloxycarbonylmethoxyphenyl)- 4,5,6,7-tetrahydro-2H-isoindole- 1,3-dione and (b) ethyl [[[[2-(4-chloro-6-methoxypyrimidin-2-yl)amino]carbonyl]amino]sulfonyl]benzoate, and an inert carrier or diluent wherein the weight proportion of the active ingredients (a) and (b) is 1:0.005 to 1.

2. The composition according to claim 1, wherein the combined content of the active ingredients is from 0.5 to 90% by weight.

3. A method for controlling weeds which comprises applying a herbicidally effective amount of the composition according to claim 1 to the weeds.

4. The method according to claim 3, wherein the weeds are those germinated in the field of peanut or soybean.

5. The method according to claim 3, wherein the combined amount of the active ingredients to be applied is from 0.2 to 4 grams per are.

6. The method according to claim 3, wherein the weeds comprise prickly sida.

* * * * *